United States Patent [19]

Smith

[11] Patent Number: 4,982,035

[45] Date of Patent: * Jan. 1, 1991

[54] COUPLING PROCESS

[75] Inventor: R. Scott Smith, Baton Rouge, La.

[73] Assignee: Ethyl Corporation, Richmond, Va.

[*] Notice: The portion of the term of this patent subsequent to May 1, 2007 has been disclaimed.

[21] Appl. No.: 372,261

[22] Filed: Jun. 27, 1989

Related U.S. Application Data

[63] Continuation-in-part of Ser. No. 276,531, Nov. 28, 1988, abandoned.

[51] Int. Cl.$^5$ .................. C07C 2/64; C07C 15/067
[52] U.S. Cl. ......................... 585/452; 585/453; 585/467
[58] Field of Search ............... 585/452, 453, 467

[56] References Cited

U.S. PATENT DOCUMENTS

| | | | |
|---|---|---|---|
| 2,771,495 | 11/1956 | Pines et al. | 585/453 |
| 2,984,691 | 5/1961 | Fotis | 585/452 |
| 3,006,976 | 10/1961 | Shaw et al. | 585/453 |
| 3,129,183 | 4/1964 | Scneider | 585/452 |
| 3,244,758 | 4/1966 | Eberhardt | 585/452 |
| 3,691,242 | 9/1972 | Cheng et al. | 260/668 B |
| 3,766,288 | 10/1973 | Shima et al. | 585/452 |
| 4,140,726 | 2/1979 | Undland et al. | 585/453 |
| 4,179,580 | 12/1979 | Cobb | 585/452 |
| 4,371,729 | 2/1983 | Shimizu | 585/453 |

FOREIGN PATENT DOCUMENTS

| | | | |
|---|---|---|---|
| 0676554 | 12/1963 | Canada | 585/452 |
| 0128001 | 1/1987 | European Pat. Off. | |

OTHER PUBLICATIONS

Eberhardt et al., "Catalytic Carbanionic Addition of Butadiene to Alkyl Aromatic Hydrocarbons", J. Org. Chem., vol. 30, pp. 82–84, 1965.

Claff et al., "Metalation of the Alpha Carbon of Alkylaryl Hydrocarbons", J. Org. Chem., vol. 20, pp. 440–442; 981–986, 1955.

*Primary Examiner*—Patrick P. Garvin
*Assistant Examiner*—E. D. Irzinski
*Attorney, Agent, or Firm*—Patricia J. Hogan; Richard J. Hammond

[57] ABSTRACT

An alkene selected from ethene, propene, and mixtures thereof is coupled with an aromatic hydrocarbon having an active hydrogen on a saturated alpha-carbon in the presence of a supported potassium or potassium alloy as a catalyst and cesium oxide as a co-catalyst. In a preferred embodiment of the invention, the active hydrogen-containing aromatic hydrocarbon is an alkylbenzene, such as toluene.

14 Claims, No Drawings

COUPLING PROCESS

CROSS REFERENCE TO RELATED APPLICATION

This application is a continuation-in-part of copending application Ser. No. 276,531, filed Nov. 28, 1988, now abandoned

FIELD OF INVENTION

This invention relates to a process for coupling ethene and/or propene with an aromatic hydrocarbon having an active hydrogen on a saturated alpha-carbon.

BACKGROUND

As disclosed, e.g., in U.S. Pat. Nos. 3,244,758 (Eberhardt) and 4,179,580 (Cobb) and in European Patent No.128001 (Kudoh et al.), it is known that supported alkali metals, including potassium and sodium-potassium alloys, are useful as catalysts in the coupling of ethylenically-unsaturated hydrocarbons with aromatic hydrocarbons having an active hydrogen on a saturated alpha-carbon. The supported alkali metals are more effective than the corresponding unsupported alkali metals in such reactions but are still not as effective as might be desired.

Claff et al., *Journal of Organic Chemistry*, Vol. 20, pp. 440–442 and 981–986 (1955) disclose the use of sodium oxide in the metalation of toluene by potassium; and the speculative teachings of U. S. Pat. No. 3,691,242 (Cheng et al.) include the substitution of an alkali metal oxide for an alkali metal alkoxide as a cc-catalyst in the alkali metal-catalyzed reaction of cumene with ethylene or propylene.

Copending application Ser. No. 356,186 (Smith), filed May 24, 1989, discloses the use of an oxide of sodium, potassium, or rubidium as a co-catalyst for the coupling of ethene and/or propene with aromatic hydrocarbons having an active hydrogen on a saturated α-carbon in the presence of a supported alkali metal as a catalyst.

SUMMARY OF THE INVENTION

An object of this invention is to provide a novel process for coupling ethene and/or propene with an aromatic hydrocarbon having an active hydrogen on a saturated alpha-carbon.

Another object is to provide such a process which utilizes a supported alkali metal as a catalyst.

A further object is to provide such a process in which the reaction rate and product yield are increased.

These and other objects are attained by coupling ethene and/or propene with an aromatic hydrocarbon having an active hydrogen on a saturated alpha-carbon in the presence of a supported potassium or potassium alloy as a catalyst and cesium oxide as a co-catalyst, the catalyst composition containing about 200–1500 weight % of support and about 4–40 mol % of co-catalyst, based on the amount of alkali metal catalyst.

DETAILED DESCRIPTION

As already mentioned, the alkene which is coupled with the aromatic hydrocarbon in the practice of the invention may be ethene, propene, or a mixture thereof. However, it is preferably propene or a propene-ethene mixture.

The aromatic hydrocarbon having an active hydrogen on a saturated alpha-carbon may be any such compound that is known to be useful in such reactions, such as toluene, ethylbenzene, n-propylbenzene, isopropylbenzene, n-butylbenzene, sec-butylbenzene, isobutylbenzene, n-eicosylbenzene, o-, m-, and p-xylenes, o-, m-, and p-ethyltoluenes, 1,3,5-trimethylbenzene, 1,2,4,5- and 1,2,3,5-tetramethylbenzenes, p-diisopropylbenzene, 1- and 2-methylnaphthalenes, dimethylnaphthalenes, 1-ethyl-4-n-octadecylnaphthalene, 1,4-di-n-pentylnaphthalene, 1,2,3,4-tetrahydronaphthalene, indan, cyclohexylbenzene, methylcyclohexylbenzene, diphenylmethane, etc. However, it is generally a hydrocarbon corresponding to the formula RR'R"CH, in which R is an aryl group of up to 20 carbons and R' and R" are independently selected from hydrogen and alkyl and aryl groups of up to 20 carbons; and it is apt preferably to be an alkylbenzene having one or more ar-alkyl groups. A particularly preferred aromatic hydrocarbon is toluene.

The mol ratio of alkene to aromatic hydrocarbon varies with the particular reactants employed and the products desired, particularly since the aromatic hydrocarbon may have one or more active hydrogens, and it may be desired to react the alkene with only one or with more than one active hydrogen in the aromatic hydrocarbon. It is frequently preferred to employ the reactants in the stoichiometric amounts appropriate for the preparation of the desired product. However, either reactant can be used in excess.

The alkali metal employed as a catalyst may be potassium or a potassium alloy, e.g., a sodium-potassium alloy having a potassium content of 40–90% by weight. As in Cobb, the teachings of which are incorporated herein in toto by reference, it appropriately has its surface area increased by being finely divided or liquid as well as by being supported on any suitable support material, such as diatomaceous earth, activated charcoal, granular coke, silica, alumina, pumice, porcelain, quartz, steel turnings, copper shot, sodium carbonate, potassium carbonate, etc. The amount of alkali metal used is a catalytic amount, generally about 2–10 mol %, based on the amount of either of the reactants when they are employed in equimolar amounts or on the amount of the major reactant when they are not utilized in equimolar amounts.

The co-catalyst of the invention is cesium oxide, which like the alkali metal, is used in finely divided form.

The reaction is conducted by heating a mixture of the alkene, the active hydrogen-containing aromatic hydrocarbon, the supported catalyst, and the co-catalyst under substantially anhydrous conditions at a suitable temperature generally about 100°–300° C., preferably about 175°–200° C., to couple the reactants. It is generally conducted in the absence of a diluent or in the presence of an excess of the active hydrogen-containing aromatic hydrocarbon as the sole diluent. However, an inert diluent can be used if desired. Exemplary of such diluents are liquid alkanes, cycloalkanes, and aromatic hydrocarbons, such as pentane, hexane, isooctane, cyclohexane, naphthalene, decahydronaphthalene, white oils, etc.

The process of the invention proceeds at a faster rate and provides higher product yields with fewer by-products than comparable processes conducted in the absence of the co-catalyst, and it is particularly advantageous as a means of alkylating alkylaromatic compounds, especially alkylbenzenes, to form compounds useful as solvents, internal standards, intermediates for polymers, pharmaceuticals, or pesticides, etc. It has the advantage over the Smith process of forming smaller amounts of methylpentene and tar-like by-products than the process utilizing an oxide of sodium, potassium, or rubidium as the co-catalyst.

The extent to which the use of both the support and the co-catalyst increases the activity of the potassium or potassium alloy catalyst is surprising. Comparison of experiments in which both the support and the co-catalyst were employed with experiments in which neither was used, experiments in which only the support was utilized, and experiments in which only the co-catalyst was utilized demonstrate that the support and co-catalyst act synergistically to provide an increase in catalytic activity that is greater than the additive effect that might have been expected from the results achieved by the use of the supports and co-catalysts separately.

The following examples are given to illustrate the invention and are not intended as a limitation thereof.

COMPARATIVE EXAMPLE A

A suitable reaction vessel was charged with 92 g (1.0 mol) of toluene, $C_{11}$ paraffin as a GC standard, and 1.0 g of NaK (an alloy having a K content of 78% by weight). The mixture was stirred and heated to 185° C. in 15 minutes, after which propene was charged until a pressure of 2758 kPa was reached; and the propene pressure was then maintained at 2689-2758 kPa throughout the reaction. Periodically the stirrer was stopped to allow the solids to settle; and samples were drawn, allowed to cool to room temperature, and subjected to GC analysis to determine the amounts of unreacted toluene, desired isobutylbenzene (IBB) product, and n-butylbenzene (NBB), methylindan (MI), and methylpentene (MP) by-products. Finally the reaction was stopped by cooling the reactor to 75° C., venting most of the propene, and injecting 10 mL of methanol under nitrogen pressure to quench the catalyst. The results of the analyses are shown below.

| Time (min.) | Mols × 100 | | | | |
| --- | --- | --- | --- | --- | --- |
| | Toluene | IBB | NBB | MI | MP |
| 40 | 100 | 0 | 0 | 0 | 0 |
| 80 | 91 | 1.8 | 0.2 | 0.01 | 0.2 |
| 160 | 83 | 9.6 | 1.0 | 0.2 | 0.9 |
| 240 | 70 | 17.2 | 1.6 | 0.5 | 1.4 |

COMPARATIVE EXAMPLE B

Comparative Example A was repeated except that 4.9 g of diatomaceous earth was included in the initial charge to the reaction vessel. The analytical results are shown below.

| Time (min.) | Mols × 100 | | | | |
| --- | --- | --- | --- | --- | --- |
| | Toluene | IBB | NBB | MI | MP |
| 0 | 100 | 0 | 0 | 0 | 0 |
| 40 | 100 | 0 | 0 | 0 | 0 |
| 80 | 93.0 | 3.5 | 0.2 | 0.46 | 0.4 |
| 120 | 78.3 | 11.3 | 0.53 | 2.56 | 1.2 |
| 160 | 66.0 | 17.4 | 0.81 | 4.12 | .1.7 |
| 200 | 62.1 | 21.2 | 0.98 | 4.90 | 2.0 |
| 240 | 60.3 | 22.8 | 1.05 | 5.18 | 2.2 |

COMPARATIVE EXAMPLE C

Comparative Example A was repeated except that 8.5 mmol of −325 mesh cesium oxide was included in the initial charge to the reaction vessel. The analytical results are shown below.

| Time (min.) | Mols × 100 | | | | |
| --- | --- | --- | --- | --- | --- |
| | Toluene | IBB | NBB | MI | MP |
| 80 | 99 | 0.1 | 0 | 0 | 0 |
| 160 | 97 | 2.2 | 0.2 | 0.1 | — |
| 240 | 77 | 12.6 | 1.3 | 0.9 | 0.5 |

EXAMPLE I

Comparative Example A was repeated except that both 4.9 g of diatomaceous earth and 8.6 mmol of cesium oxide were included in the initial charge to the reaction vessel. The analytical results are shown below.

| Time (min.) | Mols × 100 | | | | |
| --- | --- | --- | --- | --- | --- |
| | Toluene | IBB | NBB | MI | MP |
| 0 | 100 | 0 | 0 | 0 | 0 |
| 40 | — | 2.0 | 0.24 | 0.07 | 0.2 |
| 80 | 86.4 | 14.0 | 1.53 | 0.85 | 1.04 |
| 120 | 66.3 | 31.6 | 3.25 | 1.76 | 2.3 |
| 170 | 49.8 | 44.6 | 4.49 | 2.16 | 2.8 |
| 200 | 41.6 | 49.8 | 4.97 | 2.22 | 2.9 |
| 240 | 36.3 | 52.2 | 5.19 | 2.25 | 2.9 |

The amount of tar-like by-products obtained after methanol hydrolysis of the catalyst and reactor residues was determined to be 1.15 g/g of NaK and 2.20 g/mol of IBB formed.

EXAMPLE II

Example I was essentially repeated except that the amount of cesium oxide used was 4.3 mmol. The analytical results are shown below.

| Time (min.) | Mols × 100 | | | | |
| --- | --- | --- | --- | --- | --- |
| | Toluene | IBB | NBB | MI | MP |
| 0 | 100 | 0 | 0 | 0 | 0 |
| 40 | — | 1.2 | 0.13 | 0.04 | 0.1 |
| 80 | — | 5.0 | 0.55 | 0.26 | 0.5 |
| 120 | 85.6 | 16.7 | 1.92 | 0.77 | 1.3 |
| 160 | 61.2 | 35.9 | 4.21 | 1.06 | 2.9 |
| 200 | 44.6 | 51.0 | 5.86 | 1.06 | 4.3 |
| 240 | 33.3 | 58.9 | 6.57 | 1.00 | 4.9 |

The amount of tar-like by-products obtained after methanol hydrolysis of the catalyst and reactor residues was determined to be 1.71 g/g of NaK and 2.90 g/mol of IBB formed.

As can be calculated from the % conversions of toluene after 240 minutes in the preceding examples, the activity of the catalyst was increased by 32.3% by using a support in the absence of cesium oxide, decreased by 23.3% by using cesium oxide in the absence of a support, and increased by an amazing 112.3–122.3% by using both the support and the cesium oxide. The following example shows that the substitution of sodium oxide for cesium oxide in the process effects an even greater increase in catalytic activity but also increases the amount of methylpentene by-product and the tar-like by-products obtained after methanol hydrolysis of the catalyst and reactor residues.

COMPARATIVE EXAMPLE D

Example I was essentially repeated except that 8.6 mmol of −325 mesh sodium oxide was included in the initial charge to the reaction vessel instead of the cesium oxide. The analytical results are shown below.

| Time | Mols × 100 | | | | |
|---|---|---|---|---|---|
| (min.) | Toluene | IBB | NBB | MI | MP |
| 0 | 100 | 0 | 0 | 0 | 0 |
| 40 | — | 0.9 | 0.07 | 0 | 0.1 |
| 80 | 84.9 | 9.3 | 1.13 | 0.13 | 1.1 |
| 120 | 68.2 | 25.2 | 3.22 | 0.30 | 2.8 |
| 160 | 48.1 | 42.5 | 5.09 | 0.35 | 5.5 |
| 200 | 33.3 | 54.1 | 6.10 | 0.38 | 7.6 |
| 240 | 25.0 | 61.1 | 6.45 | 0.43 | 9.6 |

The amount of tar-like by-products obtained after methanol hydrolysis of the catalyst and reactor residues was determined to be 1.88 g/g of NaK and 3.13 g/mol of IBB formed.

It is obvious that many variations may be made in the products and processes set forth above without departing from the spirit and scope of this invention.

What is claimed is:

1. In a process for coupling an alkene selected from ethene, propene, and mixtures thereof with an aromatic hydrocarbon having an active hydrogen on a saturated alpha-carbon in the presence of a supported potassium or potassium alloy as a catalyst, the improvement which comprises conducting the reaction in the presence of cesium oxide as a co-catalyst, the catalyst composition containing about 200–1500 weight % of support and about 4–40 mol % of co-catalyst, based on the amount of potassium or potassium alloy.

2. The process of claim 1 wherein the alkene is a mixture of propene and ethene.

3. The process of claim 1 wherein the alkene is propene.

4. The process of claim 1 wherein the aromatic hydrocarbon is a hydrocarbon corresponding to the formula RR'R"CH, in which R is an aryl group of up to 20 carbons and R' and R" are independently selected from hydrogen and alkyl and aryl groups of up to 20 carbons.

5. The process of claim 4 wherein the aromatic hydrocarbon is an alkylbenzene.

6. The process of claim 5 wherein the alkylbenzene is toluene.

7. The process of claim 1 wherein the supported catalyst is potassium.

8. The process of claim 1 wherein the supported catalyst is a sodium-potassium alloy having a potassium content of 40–90% by weight.

9. The process of claim 1 which is conducted at a temperature of about 100°–300° C.

10. The process of claim 9 wherein the reaction temperature is about 175°–200° C.

11. The process of claim 1 wherein the support is diatomaceous earth.

12. The process of claim 1 wherein the support is potassium carbonate.

13. The process of claim 1 wherein the support is alumina.

14. The process of claim 1 wherein propene is coupled with toluene at about 175°–200° C. in the presence of a supported potassium or alloy catalyst and the co-catalyst.

* * * * *

UNITED STATES PATENT AND TRADEMARK OFFICE
CERTIFICATE OF CORRECTION

PATENT NO.   : 4,982,035
DATED        : January 1, 1991
INVENTOR(S)  : R. Scott Smith It is certified that error appears in the above-identified patent and that said Letters Patent is hereby corrected as shown below:

Column 6, line 33, reads "supported potassium or alloy" and should read --supported potassium or sodium-potassium alloy--.

Signed and Sealed this

Fourteenth Day of July, 1992

Attest:

DOUGLAS B. COMER

Attesting Officer    Acting Commissioner of Patents and Trademarks